(12) United States Patent
Wang et al.

(10) Patent No.: US 6,612,149 B2
(45) Date of Patent: Sep. 2, 2003

(54) METHOD AND APPARATUS FOR CALIBRATION OF INSTRUMENTS THAT MONITOR THE CONCENTRATION OF A STERILANT IN A SYSTEM

(75) Inventors: Jianjun Wang; David A. Mondiek, both of Dublin; Dennis V. Boruszewski, Pickerington; David P. Guntrip, Reynoldsburg, all of OH (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 09/784,710

(22) Filed: Feb. 15, 2001

(65) Prior Publication Data

US 2002/0152792 A1 Oct. 24, 2002

(51) Int. Cl.⁷ ............................................. G01N 35/08
(52) U.S. Cl. ....................................................... 73/1.02
(58) Field of Search ............................... 73/1.02, 1.06; 702/86, 104

(56) References Cited

U.S. PATENT DOCUMENTS

| | | | |
|---|---|---|---|
| 4,722,217 A | | 2/1988 | Arnett et al. |
| 5,608,156 A | | 3/1997 | Ando et al. |
| 5,659,125 A | | 8/1997 | Ernst |
| 5,741,413 A | | 4/1998 | Capetanopoulos |
| 6,171,865 B1 | * | 1/2001 | Weigl et al. ................. 436/52 |
| 6,318,151 B1 | | 11/2001 | Wang et al. |

OTHER PUBLICATIONS

Taizo, et al., "Application of a Newly Developed Hydrogen Peroxide Vapor Phase Sensor to HPV Sterilizer", *PDA Journal of Pharmaceutical Science & Technology*, vol. 52, No. 1, Jan.–Feb. 1998, pp. 13–18.

U.S. patent application Ser. No. 09/360,772, filed Jul. 26, 1999.

U.S. patent application Ser. No. 09/443,768, filed Nov. 9, 1999.

PCT Search Report

\* cited by examiner

*Primary Examiner*—Robert Raevis
(74) *Attorney, Agent, or Firm*—David L. Weinstein (57) ABSTRACT

A method and apparatus for calibrating a sensor for determination of the concentration of a sterilant, e.g., hydrogen peroxide vapor, in a sterilization system. This invention provides a method for calibrating a sensor that is used for measuring the quantity of a sterilant in a system for delivering the sterilant, the method comprising the steps of:

(a) generating reference calibration data, the reference calibration data showing a mathematical relationship between a measurable parameter, e.g. voltage, and a quantity of the sterilant, e.g., parts of sterilant per million parts of air (ppm), for a plurality of sensors;

(b) generating sensor calibration data, the sensor calibration data showing a mathematical relationship between the measurable parameter and the quantity of the sterilant for an individual sensor; and (c) normalizing the sensor calibration data to compensate for the difference between the measurable parameter for the reference calibration data and the measurable parameter for the sensor calibration data, whereby data obtained by the individual sensor can be used to accurately determine the quantity of sterilant in the system.

28 Claims, 3 Drawing Sheets

METHOD AND APPARATUS FOR CALIBRATION OF INSTRUMENTS THAT MONITOR THE CONCENTRATION OF A STERILANT IN A SYSTEM

BACKGROUND OF THE INVENTION

1. Field of the Invention

This invention relates to a method for calibration of instruments. More particularly, this invention relates to a method for calibration of instruments that monitor the concentration of a sterilant, e.g., hydrogen peroxide, in a system.

2. Discussion of the Art

Aseptic processing of consumable products, such as nutritional compounds and food products, is typically effected by separate sterilization of the products and the containers within which the products are packaged. Subsequent to sterilization, the sterilized products are placed in sterilized containers and sealed in a sterile environment for shipment, storage, and use.

Sterilization of such containers, which may include sterilization of separate closures as well, can be performed efficiently by use of a sterilant, such as hydrogen peroxide ($H_2O_2$) vapor, prior to the introduction of the desired sterilized products into the containers. In such a process, the containers are introduced into a sterilization apparatus in which the containers are flushed with hydrogen peroxide vapor. The containers are subsequently flushed with warm air or any other fluid suitable for achieving desirably low levels of residual hydrogen peroxide. This general procedure is highly effective in achieving sterilization of the containers and can be performed on any other articles that will come into contact with the material to be introduced into the containers.

Notwithstanding the effectiveness of sterilization by hydrogen peroxide, accurate monitoring of concentration levels of hydrogen peroxide vapor can be problematic. Problems in monitoring the concentration of hydrogen peroxide vapor result in part from changes in the physical and chemical properties of hydrogen peroxide vapor under processing conditions and the decomposition of hydrogen peroxide vapor upon contact with surfaces of various objects within the processing area. As such, undesired deviations of the concentration of hydrogen peroxide vapor from a process set point, along with excessive decomposition of hydrogen peroxide vapor, can result in loss of sterility of the containers and surrounding aseptic processing area. Moreover, hydrogen peroxide vapor is corrosive in nature, and thus excessive concentration levels of hydrogen peroxide may bring about detrimental effects to the equipment in and surrounding the processing area and surfaces of objects within the processing area. Furthermore, in accordance with government standards, subsequent use of sterilized containers requires low levels of residual sterilant.

Heretofore, detection systems for hydrogen peroxide vapor have been undesirably bulky, as exemplified by conventional near infrared (NIR) analysis apparatus. In addition, current off-line testing methods are typically too slow for monitoring levels of sterilant with sufficient accuracy. Previous arrangements have not allowed real time monitoring throughout an aseptic processing cycle, and in particular, have not been capable of monitoring concentrations of hydrogen peroxide vapor within the sterilization apparatus at select locations along the sterilant supply system during actual operations. However, U.S. Pat. No. 5,608, 156 and Taizo et al., "Application of a Newly Developed Hydrogen Peroxide Vapor Phase Sensor to HPV Sterilizer", PDA Journal Of Pharmaceutical Science & Technology, Vol. 52, No. 1/January—February 1998, pp. 13–18, describe methods of detecting the concentration of hydrogen peroxide vapor and an apparatus therefor that appear to address some of the foregoing problems.

The concentration of sterilants detected within a system is generally a function of various environmental parameters, such as, for example, temperature, relative humidity, and various measurement conditions, such as, for example, proximate location of measurement. Conventional detection systems for sterilant typically cannot or do not account for fluctuations of environmental parameters and measurement conditions. However, such fluctuations can substantially affect the results of signal generation and data collection when commercially available sensors and equipment are used. It is therefore beneficial to maintain operating parameters proximate the location of measurement as uniform as possible during data collection.

U.S. Ser. No. 09/443,768, filed Nov. 9, 1999, entitled STERILANT MONITORING ASSEMBLY AND APPARATUS AND METHOD USING SAME, incorporated herein by reference, describes an integrated system for determining the concentration of hydrogen peroxide for aseptic process validation, control, and monitoring. This system is compact and can be used for on-line determination of the concentration of hydrogen peroxide. The system requires a unique calibration procedure at regular intervals to guarantee reliable and accurate test results. This system utilizes a sensor having elements made of $SnO_2$. When $SnO_2$ is heated to a high temperature, around 400° C., in the absence of oxygen, free electrons flow easily through the grain boundary of the $SnO_2$ particles. In clean air, oxygen, which traps free electrons by its electron affinity, is adsorbed onto the surface of the $SnO_2$ particle, forming a potential barrier in the grain boundaries that restricts the flow of electrons, thereby causing the electronic resistance to increase. When the sensor is exposed to hydrogen peroxide vapor, $SnO_2$ adsorbs its gas molecules and causes oxidation. This lowers the potential barrier, allowing electrons to flow more easily, thereby reducing the electrical resistance. Thus, the sensor uses an indirect method to measure the concentration of hydrogen peroxide vapor.

Voltage data from the output of the sensor must be compared to a database derived from a calibration process. The output of two different sensors cannot be compared directly without calibration. The calibration procedure uses several representative points (i.e., concentration at a given voltage) to establish a mathematical relationship that covers a specific test window. Only by means of calibration can the output voltage of a sensor be converted to a value of concentration.

Calibration procedures are important for minimizing deviations caused by such components as semiconductor chips, batteries, and signal conditioning circuits in a sensor in a portable detection system. Calibration procedures are important for minimizing deviations caused by such components as temperature and humidity compensation circuits, heating coils, data recording systems, and memory chips in a sensor in a fixed detection system.

If the calibration method is not reliable, the concentration of hydrogen peroxide vapor detected by a sensor might be misleading. In turn, an erroneous determination of the concentration of hydrogen peroxide vapor can bring about contamination in the operation system and result in spoilage.

For example, a drop in voltage in the response of the sensor caused by an increase in the rate of flow of air may be interpreted as a decrease in the concentration of hydrogen peroxide vapor in the system. This apparent decrease may cause the controls in the system to increase the quantity of hydrogen peroxide delivered, thereby providing an excessive amount of hydrogen peroxide vapor. An excessive amount of hydrogen peroxide in the system may result in an excessive amount of residue. Conversely, an increase in voltage in the response of the sensor may result from a decrease in the rate of flow of air. If the delivery rate of hydrogen peroxide is correspondingly reduced, a breach in the sterility of the system may occur.

Calibration of sensors one at a time is inefficient, and, consequently, costly. It is well-known that no two sensors chosen at random are likely to be identical. Accordingly, it would be desirable to find way to calibrate individual sensors accurately and at reasonable cost. In addition, it would be desirable to find a way to calibrate individual sensors so that one or more of them could be used in portable units. The use of a greater number of portable units is desirable so that measurement of the concentration of hydrogen peroxide can be made at any point in a production line.

SUMMARY OF THE INVENTION

This invention provides a method and apparatus for calibrating a sensor for determination of the concentration of a sterilant, e.g., hydrogen peroxide vapor, in a sterilization system.

In one aspect, this invention provides a method for calibrating a sensor that is used for measuring the quantity of a sterilant in a system for delivering the sterilant, the method comprising the steps of:

(a) generating reference calibration data, the reference calibration data showing a mathematical relationship between a measurable parameter, e.g. voltage, and a quantity of the sterilant, e.g., parts of sterilant per million parts of air (ppm), for a plurality of sensors;

(b) generating sensor calibration data, the sensor calibration data showing a mathematical relationship between the measurable parameter and the quantity of the sterilant for an individual sensor; and (c) normalizing the sensor calibration data to compensate for the difference between the measurable parameter for the reference calibration data and the measurable parameter for the sensor calibration data, whereby data obtained by the individual sensor can be used to accurately determine the quantity of sterilant in the system.

The reference calibration data can be generated by a method comprising the steps of:

(a) providing a plurality of sensors;

(b) subjecting each of the plurality of sensors to at least two quantities of air (e.g., 30 cubic meters/hour and 110 cubic meters/hour), each of the at least two quantities of air having (1) a known quality (e.g., 60% relative humidity at 70° C.) and (2) a known concentration of sterilant vapor (e.g., 10,000 ppm of hydrogen peroxide vapor), the sterilant vapor having a known physical condition (e.g., 70° C.);

(c) measuring the signals (e.g., voltage) emitted by each of the plurality of sensors, each of the signals being proportional to a concentration (e.g., ppm) of sterilant vapor;

(d) establishing a mathematical relationship between the signals emitted by each of the plurality of sensors and the concentrations of sterilant vapor for each of the plurality of sensors; and (e) establishing the reference calibration data by means of a statistical analysis of the signals emitted by each of the plurality of sensors and the concentrations of sterilant vapor for each of the plurality of sensors.

The sensor calibration data can be generated by a method comprising the steps of:

(a) providing a sensor;

(b) subjecting the sensor to at least two quantities of air, each of the at least two quantities of air having (1) a known quality and (2) a known concentration of sterilant vapor, the sterilant vapor having a known physical condition;

(c) measuring the signals (e.g., voltage) emitted by the sensor, each of the signals corresponding to a concentration of sterilant vapor (e.g., ppm of hydrogen peroxide vapor); and (d) establishing a mathematical relationship between the signals emitted and the concentrations of sterilant vapor for the sensor.

The sensor calibration data can be normalized to compensate for the difference between the measurable parameter for the reference calibration data (e.g., voltage) and the measurable parameter for said sensor calibration data for the sensor (e.g., voltage) by a method comprising the steps of:

(a) selecting a concentration of sterilant vapor;

(b) determining the value of the measurable parameter at which the concentration of the sterilant vapor obtained from the sensor calibration data equals the concentration of said sterilant vapor obtained from the reference calibration data; and (c) adjusting the values measured by the individual sensor a sufficient amount to compensate for the deviation between the reference calibration data and the sensor calibration data.

The method of this invention brings about a reduction in the time required to calibrate a sterilization system and provides a means for directly comparing signals obtained from different sensors so that the complex steps involved in the indirect measurement of parameters are avoided.

In one embodiment, which is relatively simple to implement, a linear relationship between the measured signal (e.g., voltage) and the concentration of sterilant (e.g., ppm of hydrogen peroxide vapor) is assumed. Points on the curve for an individual sensor (i.e., sensor calibration data) are moved either vertically or rotationally or both in order to convert the values of concentration associated with that point to a value of concentration on the curve representing the reference calibration data.

The form of the data for calibration of sensors for determining the concentration of hydrogen peroxide vapor in a stream of air is not critical. Preferred forms for presentation of data include, but are not limited to, curves plotted on Cartesian coordinates, nomograms, and look-up tables containing signal/concentration data.

In one embodiment, in which curves plotted on Cartesian coordinates are employed, the method involves the steps of (a) preparing a reference calibration curve, the reference calibration curve having a slope and an intercept;

(b) preparing a sensor calibration curve, the sensor calibration curve having a slope and an intercept; and (c) normalizing the sensor calibration curve to compensate for (1) the difference between the slope of the reference calibration curve and the slope of the sensor calibration curve and (2) the difference between the intercept of the reference calibration curve and the intercept of the sensor calibration curve.

For this embodiment, the reference calibration curve is prepared by a method comprising the steps of:

(a) providing a plurality of sensors;

(b) subjecting each sensor of the plurality of sensors to at least two quantities of air, each of the at least two quantities of air having (i) a known quality and (ii) a known concentration of sterilant vapor, the sterilant vapor having a known physical condition;

(c) measuring the signals emitted by each of the plurality of sensors, each of the signals being proportional to the concentration of sterilant vapor;

(d) establishing a linear mathematical relationship between the signals emitted by each of the plurality of sensors and the concentrations of sterilant vapor for each of the plurality of sensors; and (e) establishing the reference calibration curve by means of a statistical analysis of the signals emitted by each of the plurality of sensors and the concentrations of sterilant vapor for each of the plurality of sensors.

For this embodiment, the sensor calibration curve is prepared by a method comprising the steps of:

(a) providing an individual sensor;

(b) subjecting the sensor to at least two quantities of air, each of the at least two quantities of air having (1) a known quality and (2) a known concentration of sterilant vapor, the sterilant vapor having a known physical condition;

(c) measuring the signals emitted by the sensor, each of the signals being proportional to the concentration of sterilant vapor; and (d) establishing a linear mathematical relationship between the signals emitted by the individual sensor and the concentrations of sterilant vapor for the individual sensor.

The sensor calibration curve is normalized to compensate for (1) the difference between the slope of the reference calibration curve and the slope of the sensor calibration curve and (2) the difference between the intercept of the reference calibration curve and the intercept of the sensor calibration curve by a method comprising the steps of:

(a) determining the intercept of the reference calibration curve;

(b) determining the intercept of the sensor calibration curve;

(c) determining the slope of the reference calibration curve;

(d) determining the slope of the sensor calibration curve;

(e) adjusting the sensor calibration curve, if necessary, in order to compensate for the difference between the intercept of the reference calibration curve and the intercept of the sensor calibration curve; and (g) adjusting the sensor calibration curve, if necessary, in order to compensate for the difference between the slope of the reference calibration curve and the slope of the sensor calibration curve.

In another aspect, this invention provides a method for calibrating a portable unit for measuring the concentration of hydrogen peroxide. In this method, hydrogen peroxide vapor can be passed through a calibration vessel, which is submerged in a water bath, under controlled testing conditions. A portable sensor for the detection of hydrogen peroxide vapor installed within the calibration vessel will respond to the concentration of hydrogen peroxide, the temperature, and the relative humidity for each test run. The concentration of hydrogen peroxide can be rechecked by a standard titration method. The accuracy of the value of the concentration of hydrogen peroxide thus determined can be checked by means of a detection unit for hydrogen peroxide vapor residue (Drager kit) to determine the concentration of residual hydrogen peroxide in the flow stream exiting the system. Additional impingers can be added to the system to capture all hydrogen peroxide from the stream of flowing air if residual hydrogen peroxide should be detected by a detection unit for hydrogen peroxide vapor residue. Additional data can be generated to cover those conditions that would be expected to be encountered in a practical application.

The method of this invention is capable of conducting calibrations that mimic both static and dynamic processing conditions, such as seen in sterilization of Bosch aseptic machines and hydrogen peroxide spray sterilization of bottles. Flexibility in the selection of parameters encountered in the generation of hydrogen peroxide vapor allows dynamic and static calibration of instruments for the determination of the concentration of hydrogen peroxide under conditions of high temperature, high concentration, variable rate of flow of air, and variable humidity for the test cell.

The method of this invention allows the calibration of instruments for determining the concentration of hydrogen peroxide vapor for numerous applications. The combined application of a water bath, a titration station, a Drager kit, a metering pump, and a hydrogen peroxide flow meter allows calibration of a portable detection unit for the determination of low concentrations of hydrogen peroxide.

The method of this invention can also be used to investigate the condensation of hydrogen peroxide by changing the rate of injection of hydrogen peroxide, the temperature(s) of the heat exchanger(s), the temperature(s) of the water bath(s), and the rates of flow of air. The rates of condensation and decomposition of hydrogen peroxide can be calculated by determining the difference between the amount of hydrogen peroxide injected and the amount of hydrogen peroxide detected over a selected period of time. The temperature at which air can be saturated by hydrogen peroxide under known conditions can be estimated as well.

The method of this invention can be used to calibrate a sensor for a sterilization system to improve the ability to determine the concentration of sterilant at a given point in the system at any time at various processing stages. By this method, accurate information on the process at each stage can be provided.

The method of this invention can also be used to calibrate instruments for monitoring the concentration of hydrogen peroxide vapor in any environment where hydrogen peroxide vapor is employed. Such environments include, but are not limited to, clean room operations, pharmaceutical isolator sterilization, aseptic processing systems, and microbiological investigation of death rate for various bacteria under the effect of hydrogen peroxide.

This invention provides a method for calibrating instruments for determining the concentration of a sterilant, e.g., hydrogen peroxide vapor, for a wide range of processing and operating conditions. These operating condition include, but are not limited to, air temperature, flow rate of air, evaporation temperature, hydrogen peroxide injection rate, degree of saturation of air by hydrogen peroxide vapor at different temperatures, humidity variations, pressure fluctuations, etc.

It is to be understood that the method of this invention is not limited to the sterilant hydrogen peroxide. The method of this invention can be used to calibrate instruments for determining the concentration of other gases used for sterilization.

DETAILED DESCRIPTION

As used herein, the term "sterilant" means a substance that can kill one or more target microorganisms. The expression "reference calibration data" means set of data, derived from examining a plurality of sensors, used to construct a database. The set of data is obtained from at least the minimum number of a plurality of sensors that will provide a statistically significant result. The expression "measurable parameter" means a variable that can be measured by a method of measurement acceptable to one of ordinary skill in the art. The term "quantity" means the property or aspect of a thing that can be measured, counted, or compared, such as, for example, rate of flow of air. The expression "sensor calibration data" means set of data, derived from examining an individual sensor, used to construct a database. The set of data is obtained from a single sensor at a given physical condition and at a given concentration level. The term "normalizing" means causing the sensor calibration data to conform to the reference calibration data. The expression "air quality" means the physical condition of the air into which hydrogen peroxide is vaporized. Parameters that can be used to characterize air quality include, but are not limited to, temperature, relative humidity, pressure, and the like. The term "signal" means a fluctuating electric quantity, as voltage, current, electric field strength, whose variations represent coded information. The expression "mathematical relationship" means a mathematical equation that expresses at least one parameter as a function of at least one other parameter. The term "slope" means the rate at which an ordinate of a point of a line on a coordinate plane changes with respect to a change in the abscissa. The term "intercept" means the distance from the origin of coordinates along a coordinate axis to the point at which a line, a curve, or a surface intersects the axis. The expression "Drager kit" means a unit for detecting the concentration of residual hydrogen peroxide vapor. The expression "static condition" refers to the situation in which both the sensor and the hydrogen peroxide vapor are momentarily sealed in an air-tight chamber maintained at a constant temperature and humidity during a test run or calibration run. The expression "dynamic condition" refers to the situation in which the sensor is installed in the stream in which the hydrogen peroxide vapor flows.

In one aspect, this invention involves a method for calibrating a sensor that is used for measuring the quantity of a sterilant in a system for delivering the sterilant, the method comprising the steps of:

(a) generating reference calibration data, the reference calibration data showing a relationship between a measurable parameter, e.g. voltage, and a quantity of the sterilant, e.g., parts of sterilant per million parts of air (ppm), for a plurality of sensors;

(b) generating sensor calibration data, the sensor calibration data showing a relationship between the measurable parameter and the a quantity of the sterilant for an individual sensor;

(c) normalizing the sensor calibration data to, compensate for the difference between the, measurable parameter for the reference calibration data and the measurable parameter for the sensor calibration data for the individual sensor, whereby the quantity of sterilant in the system can be accurately determined.

In order to generate the reference calibration data, each of a plurality of sensors is subjected to at least two quantities of air (e.g., 30 cubic meters/hour and 110 cubic meters/hour). Each of the at least two quantities of air has (1) a known quality (e.g., 60% relative humidity at 70° C.) and (2) a known concentration of sterilant vapor (e.g., 10,000 ppm of hydrogen peroxide vapor). The sterilant vapor also has a known physical condition (e.g., 70° C.). The signals emitted by each of the sensors are measured. Each of the signals measured corresponds to the concentration of sterilant vapor. Then, a mathematical relationship is established between the signals measured and the concentrations corresponding to the measured signals for each of the sensors. The foregoing operations are repeated until a mathematical relationship between the signals measured and the concentrations corresponding to the measured signals has been established for each sensor of the plurality of sensors. Then, the reference calibration data is derived from the data and mathematical relationships obtained from the foregoing measurements. Typically, the reference calibration data represents the mean (average) of the data obtained from the foregoing measurements. The number of sensors used to prepare the reference calibration data is preferably sufficient to provide reference calibration data that exhibits a normal distribution with about 95% of the values of the sensors falling within two standard deviations of the mean. In general, it is preferred that at least 10 sensors be used to provide data for preparing the reference calibration data.

In order to generate the sensor calibration data, an individual sensor is provided. This sensor is subjected to at least two quantities of air, each of the at least two quantities of air having (1) a known quality and (2) a known concentration of sterilant vapor. The sterilant vapor has a known physical condition. The signals emitted by the sensor are measured. Each of the measured signals corresponds to a concentration of sterilant vapor. A mathematical relationship is established between the signals emitted by the sensor and the concentrations corresponding to the signals measured for the sensor. Then, the sensor calibration data is derived from the data and mathematical relationships obtained from the foregoing measurements Then the sensor calibration data is normalized to compensate for the difference between the measurable parameter for the reference calibration data (e.g., voltage) and the measurable parameter for the sensor calibration data for the individual sensor. In order to carry out the normalization step, a concentration of sterilant vapor is selected. The value of the measurable parameter at which the concentration of the sterilant vapor obtained from the sensor calibration data equals the concentration of said sterilant vapor from the reference calibration data is determined. This value of the measurable parameter for a given concentration must be in both the reference calibration data and the sensor calibration data. The values of the measurable parameter in the sensor calibration data are adjusted a sufficient amount to compensate for the deviation of the sensor calibration data from the reference calibration data.

The form of the data for both the reference calibration data and the sensor calibration data is not critical. Preferred forms of data include, but are not limited to, curves plotted on Cartesian coordinates, nomograms, and tables containing signal/concentration data. Of course, the form for the reference calibration data and the sensor calibration data must be the same in order to ensure a meaningful adjustment.

In one embodiment, in which curves plotted on Cartesian coordinates are employed, the calibration can be carried out in the following manner. A linear reference calibration curve having a slope and an intercept is prepared. The value of the concentration is plotted on the abscissa and the value of signal is plotted on the ordinate. A linear sensor calibration curve for an individual sensor having a slope and an intercept is prepared. The value of the concentration is plotted on the abscissa and the value of signal is plotted on the ordinate. The reference calibration curve and the sensor calibration curve intersect at a set of coordinates. The sensor calibration curve is normalized to the reference calibration curve to compensate for (1) the difference between the slope of the reference calibration curve and the slope of the sensor calibration curve and (2) the difference between the intercept of the reference calibration curve and the intercept of the sensor calibration curve.

Normalization can be carried out in several ways. In one embodiment of normalization, the sensor calibration curve can be adjusted physically, by adjusting it vertically and rotationally so that the intercept and the slope of the sensor calibration curve conform to the intercept and the slope, respectively, of the reference calibration curve. In another embodiment of normalization, the variable representing the signal on the sensor calibration curve (i.e., voltage or log (voltage)) can be substituted into the equation that relates the concentration and the signal on the reference calibration curve.

Figure 1:
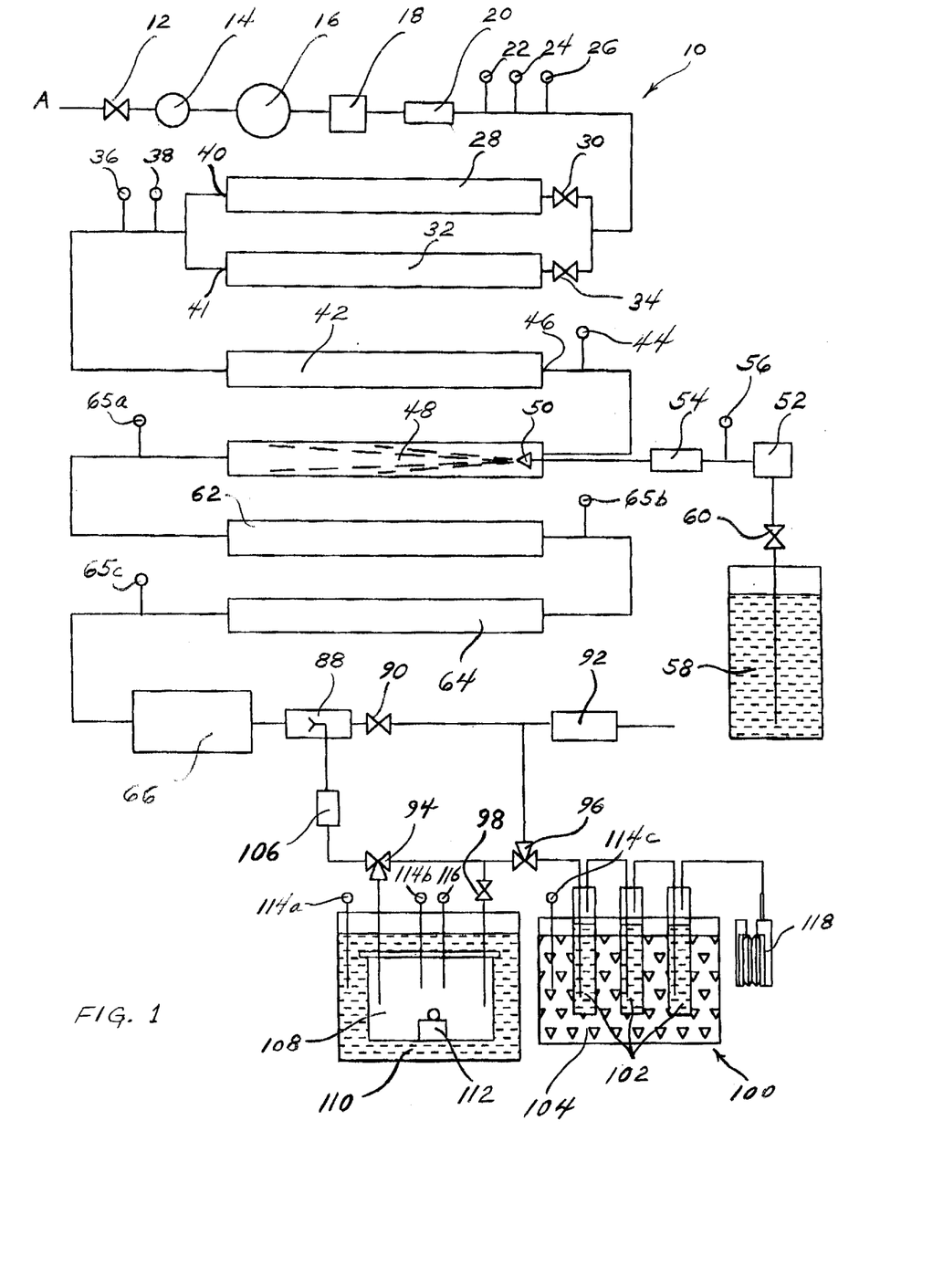
FIG. 1 is a schematic diagram that illustrates a system suitable for generating hydrogen peroxide vapor under controllable operating conditions. This diagram includes the components of the system that are needed to calibrate a sensor for a sterilization system.
Figure 2:
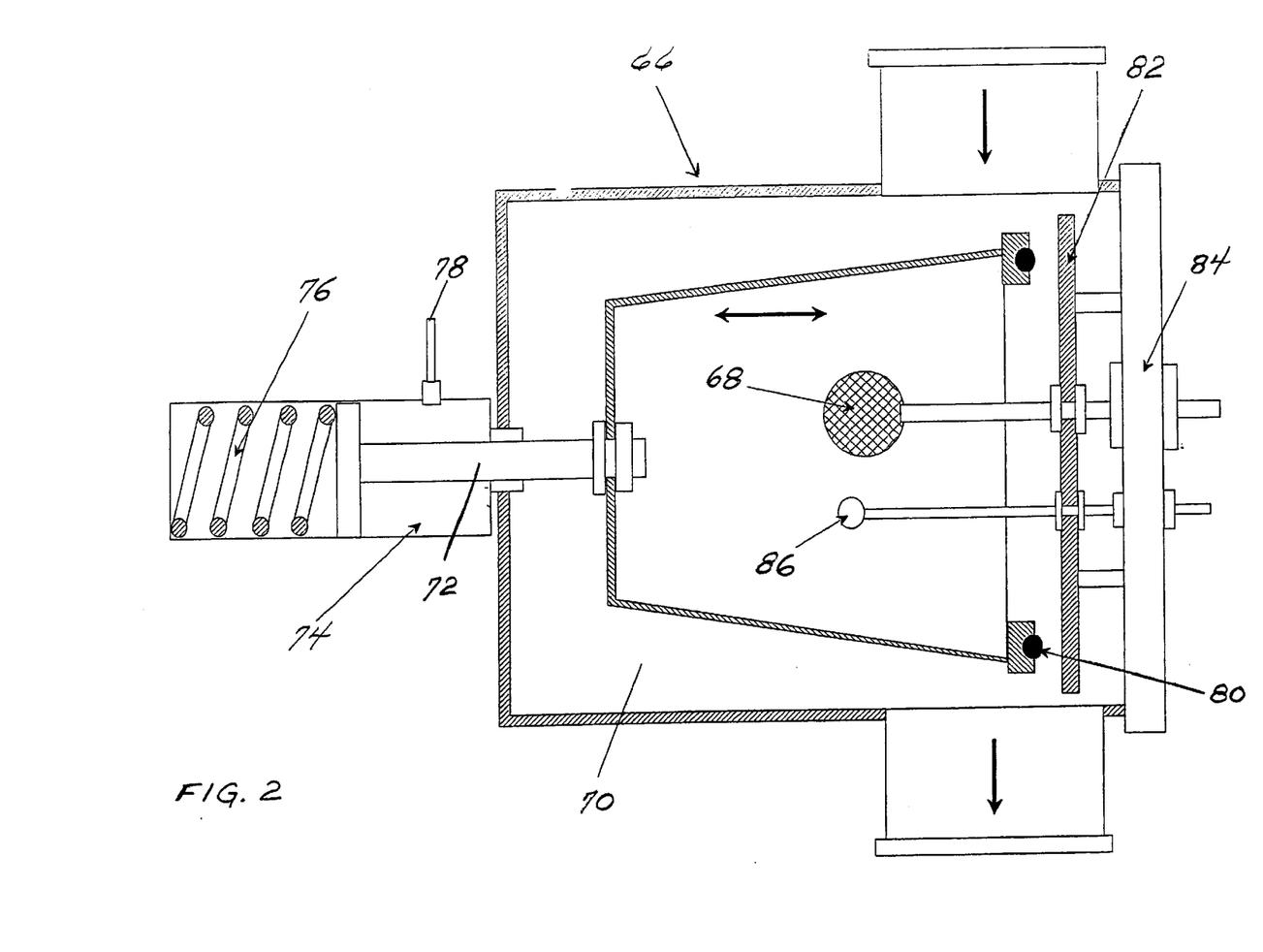
FIG. 2 is a schematic diagram that illustrates a test cell for use in calibration of a sensor for a sterilization system.

Referring now to FIGS. 1 and 2, compressed air at room temperature is introduced into a system 10 suitable for generating hydrogen peroxide vapor under controllable operating conditions by means of a valve 12. The compressed air is represented by the letter "A". The air is filtered by means of an air filter 14 to remove dirt and other foreign substances. A valve 16, preferably a diaphragm valve, is used to control the flow rate of the air, and a pressure regulator 18 is used to adjust the pressure of the air. The rate of flow of the air is monitored by a flow meter 20 and the parameters of air quality are measured and recorded by a data acquisition system (e.g., Keithley 500 data acquisition system, Keithley Instruments, Inc., 28775 Aurora Rd., Cleveland, Ohio 44139). The parameters of air quality include temperature, humidity, and pressure. These parameters are monitored by a temperature sensor 22, a humidity sensor 24, and a pressure sensor 26, respectively. Because of seasonal variations in the quality of air in the room containing the components of the system 10, the moisture content of the air is adjusted to a predetermined level for the purpose of the calibration. The moisture content of the air is adjusted by using either a dehumidifier 28, which is operated by opening or closing a valve 30, or a humidifier 32, which is operated by opening or closing a valve 34. The adjusted air quality is measured by means of a temperature sensor 36 and a humidity sensor 38 located downstream of the exit port 40 of the dehumidifier 28 and the exit port 41 of the humidifier 32. Accordingly, the temperature level and the humidity level of the air will be known.

The air is then heated to a specified temperature by means of a heat exchanger 42. The concentration of hydrogen peroxide (hereinafter $H_2O_2$) vapor in a sample of air saturated with $H_2O_2$ vapor is a function of temperature. As the temperature of the air is increased, the air can hold a higher concentration of $H_2O_2$ vapor. The temperature of the air can be monitored by a temperature sensor 44 located downstream of the exit 46 of the heat exchanger 42. In the heat exchanger 42, temperature is a function of steam pressure. By adjusting the steam pressure of the heat exchanger 42, the temperature of the air can be controlled. The air is then introduced into a heat exchanger 48 and merged with a stream of $H_2O_2$ droplets created by an atomizer 50. The $H_2O_2$ is caused to evaporate rapidly and is further heated to a higher temperature. A metering pump 52 controls the rate of injection of liquid $H_2O_2$ into the air flowing into the heat exchanger 48. A flow meter 54 is used to monitor the flow rate of liquid $H_2O_2$ to ensure that the rate of injection of $H_2O_2$ is correct. The temperature of the liquid $H_2O_2$ can be measured by a temperature sensor 56 to ensure a consistent temperature for all calibration operations. A tank for storing the liquid $H_2O_2$ is designated by the reference numeral 58, and a valve for controlling the injection of liquid $H_2O_2$ into the stream of air is designated by the reference numeral 60. The tank 58 and the valve 60 are those conventionally used for introducing liquid $H_2O_2$ into a sterilization system. Accordingly, the tank 58 and the valve 60 are resistant to $H_2O_2$.

The mixture of air and $H_2O_2$ vapor—may be in one of several conditions. These conditions may be described as follows:

1. Air is saturated with $H_2O_2$ vapor—condensation of droplets of the $H_2O_2$ vapor occurs when temperature decreases;
2. Air is not saturated with $H_2O_2$ vapor—$H_2O_2$ vapor decomposes on the surfaces of certain materials; $H_2O_2$ vapor condenses when temperature drops below the saturation temperature;
3. Under both conditions (saturated and unsaturated), if the temperature increases, $H_2O_2$ droplets will revaporize;
4. Latent heat of evaporation of $H_2O_2$ is positive; evaporation of $H_2O_2$ generates extra heat in the system. The temperature of the air is generally higher than the temperature at which the heat exchanger 48 is set, and the temperature of the air is difficult to predict and control.

Two additional heat exchangers 62 and 64 can be used to reduce the temperature of the air and ensure that the air is saturated with $H_2O_2$ vapor at a known temperature. For the air to reach a state of saturation, it is common to evaporate a liquid at a high temperature and then reduce the temperature. If a sufficient quantity of liquid is injected into the system at a high temperature, saturation can be guaranteed when the vapor is cooled. Also, the saturation process should be conducted at the last possible point before the $H_2O_2$ vapor is to be used for sterilization, because it is difficult to control condensation and decomposition at some other point in the system.

The temperature of the air at various locations in the system 10 can be monitored by temperature sensors 65a, 65b, and 65c.

The air containing the $H_2O_2$ is then introduced into a test cell 66. A simplified diagram of the test cell 66 is shown in FIG. 2. The test cell 66 is described in U. S. Ser. No. 09/443,768, filed Nov. 19, 1999, entitled STERILANT MONITORING ASSEMBLY AND APPARATUS AND METHOD USING SAME, incorporated herein by reference. In U.S. Ser. No. 09/443,768, the test cell is referred to as a sterilant monitoring assembly and is designated by the reference numeral 200. A sensor 68 suitable for determining the concentration of $H_2O_2$ vapor is installed in the test cell 66 in order to be calibrated. It is preferred that the conditions within the test cell 66 be substantially identical to those used in an actual sterilization process. It should be noted that the data for the calibration operation is likely to be valid only after the system 10 reaches a state of equilibrium. Accordingly, the system 10 should be run a sufficient amount of time in order to reach a state of equilibrium.

It is preferred that two types of runs be performed in each calibration operation. In a static test run, an internal cell 70 in the test cell 66 is placed in fluidic communication with the flowing stream of air for a specified amount of time, the flowing stream of air having reached a state of equilibrium. In order to determine the concentration of $H_2O_2$ vapor in a sample of air, the internal cell 70 in the test cell 66 is then sealed by means of a piston 72 moving in a cylinder 74 under the force of compressed air pushing against a spring 76. The compressed air can be introduced to the cylinder 74 through an inlet 78. An $H_2O_2$-resistant O-ring 80 can be used to ensure that the internal cell 70 is sealed against a heat isolation plate 82. The cover of the test chamber 66 is designated by the reference numeral 84 and a thermocouple is represented by the reference numeral 86. The data obtained by means of this static test run reflects the level of concentration of $H_2O_2$ vapor, independent of the rate of flow of air. The flowing air surrounding the internal cell 70 serves as an insulating jacket to maintain a uniform and constant temperature during the static test run. In a dynamic test run, the internal cell 70 is placed in fluidic communication with the flowing air at all times. In other words, the internal cell 70 is not sealed against the heat isolation plate 82. In the dynamic test run, the data obtained only reflect the concentration of $H_2O_2$ vapor at a specific flow rate of air.

The results obtained from the two types of calibration runs can be used to verify the determination of the concentration of $H_2O_2$ vapor under actual sterilization conditions. For example, if the readings of concentration of $H_2O_2$ vapor determined in static test runs remain substantially constant, but if the readings of concentration of $H_2O_2$ vapor determined in dynamic test runs vary substantially, (1) the flow rate of the air may have changed, (2) the rate of addition of sterilant to the system may have changed, or (2) something may be wrong with the system. Similarly, if the readings of concentration of $H_2O_2$ vapor determined in static runs conditions vary substantially, but if the readings of concentration of $H_2O_2$ vapor determined in dynamic test runs remain substantially constant, (1) the flow rate of the air may have changed, (2) the rate of addition of sterilant to the system may have changed, or (2) something may be wrong with the system. Assuming that the flow rate of the air has not changed, and that the rate of addition of sterilant to the system has not changed, what may be wrong with the system is that the sensor for determining the concentration of $H_2O_2$ vapor is providing unreliable readings, which may be the result of unreliable calibration. If the method for calibrating the sensor is unreliable, the concentration of $H_2O_2$ vapor determined by the sensor may be misleading. An erroneous determination of the concentration of $H_2O_2$ vapor can result in contamination of the system and result in spoilage of product. For example, a drop in voltage in the response measured by the sensor caused by an increase in the rate of flow of air may be interpreted as a decrease in concentration of $H_2O_2$ vapor in the system. This apparent decrease in response may cause controls in the system to increase the quantity of $H_2O_2$ delivered, thereby providing an excessive amount of $H_2O_2$ vapor.

An excessive amount of $H_2O_2$ in the system will result in an excessive amount of residue. Conversely, an increase in voltage in the response of the sensor may result from a decrease in the rate of flow of air. If the delivery rate of $H_2O_2$ is correspondingly reduced, a breach in the sterility of the system may occur. For the foregoing reasons, it is frequently desirable to cross-check calibration runs of sensors.

As stated previously, the system 10 should be run a sufficient amount of time in order to reach a state of equilibrium. When the system is activated initially, the air exiting the test cell 66 flows into a sample collection port 88 positioned downstream from the test cell 66. A valve 90 is operated to allow the air flowing through the sample collection port 88 to be transported to a catalytic converter 92, which accelerates the decomposition of $H_2O_2$ (i.e., breakdown of $H_2O_2$) before it enters the ambient environment. During this initial activation period, a valve 94, preferably a programmable three-way valve, allows air to flow through the system 10 to a valve 96, preferably a three-way valve, and from there to the catalytic converter 92. During this initial activation phase, a valve 98, which will be described later, is closed.

After the initial activation phase, i.e., when the system 10 has reached a state of equilibrium, the signal (e.g., voltage data) obtained from the sensor 68 is correlated with the concentration of $H_2O_2$ vapor in the test cell 66. In order to perform this correlation, a sample of air collected via the sample collection port 88 is passed through a titration station 100, which comprises a series of impingers 102 set in an ice bath 104. The flow rate of the sample of air is measured by a flow meter 106; the duration of the test is precisely controlled by the operation of the valve 94. In order to perform this measurement, the valve 94 allows air to flow through the system 10 to the valve 96, which is operated to allow the air to enter the titration station 100. The valve 90 is operated to allow air to flow to the catalytic converter 92, and the valve 98 is closed. The amount of $H_2O_2$ captured in the impingers 102 is a function of time. By measuring the time consumed and the amount of $H_2O_2$ collected in the impingers 102, the concentration of $H_2O_2$ can be estimated. For example, if the flow of air is 10 cubic meters per minute, and if approximately 10 mL of $H_2O_2$ vapor condense in the impingers 102, then the concentration of $H_2O_2$ is equal to approximately 1 mL per cubic meter. The rate of flow of the sample of air to the titration station 100 can be controlled by adjusting the size of an orifice in the sample collection port 88.

When the titration station 100 is used to determine the concentration of $H_2O_2$ in the sample of air in the test cell 66, the valve 94 is operated to allow the air containing the $H_2O_2$ vapor to bypass a test chamber 108 in a water bath 110. The test chamber 108 can be used to calibrate a portable $H_2O_2$ detection unit 112. A portable $H_2O_2$ detection unit is one that can be installed in a bottle sterilizer, such as, for example, a Bosch apparatus, or that can be placed at any location in an isolator or a clean room to monitor sterilization by $H_2O_2$. A portable $H_2O_2$ detection unit can also be installed inside a container, such as a 32-ounce plastic container, to detect the $H_2O_2$ vapor condition after an $H_2O_2$ vapor spraying procedure for sterilization of bottles. The portable unit is an integrated unit comprising an $H_2O_2$ sensor, a data recording element, a battery for power supply, a signal conditioning circuit, a near infrared (NIR) receiver, a DC/DC converter, and a temperature sensor. Portable units are preferably programmable, and the data obtained by using such a unit can downloaded after a test. A portable unit has a size of about 1 inch by 2 inches by 2 inches. Portable $H_2O_2$ detection units are described in U.S. Ser. No. 09/360,772, filed Jul. 26, 1999, entitled SELF-CONTAINED STERILANT MONITORING ASSEMBLY AND METHOD OF USING SAME, incorporated herein by reference. Before measurements are performed in the test chamber 108, it is preferred that the system 10 be run for a sufficient amount of time to avoid condensation of $H_2O_2$. Such condensation results from the temperature differential between the air containing the $H_2O_2$ vapor and the internal surfaces of pipes, the test cell 66, the test chamber 108, and the valves. During the initial activation phase that is suggested prior to utilizing the test chamber 108, the valve 94 is operated to allow air to flow into the test chamber 108, and the valve 98 is open. The valve 96 is operated to allow the air that exits from the test chamber 108 to flow to the catalytic converter 92, and the valve 90 is open. When the test chamber is used to calibrate a portable detection unit 112, the valve 96 is operated to prevent the air that exits from the test chamber 108 from flowing to the catalytic converter 92, and the valve 90 is open. The valve 96 is operated to allow the air that exits from the test chamber 108 to flow to the titration station 100.

During the calibration of the portable unit 112, the portable unit 112 is placed inside the test chamber 100 and operated by a remote control (not shown), preferably a near infrared (NIR) remote control. The flow of air is adjusted by adjusting the size of the orifice of the sample collection unit 88. The temperature of the water bath 110 is the same as the temperature of the sample of air containing the $H_2O_2$ vapor. By measuring the duration of the run and the flow rate of the sample of air, the concentration of $H_2O_2$ vapor in the sample can be calculated in the same manner as was used to calibrate the sensor 68 tested in the test cell 66. A relationship between the voltage data obtained from the portable $H_2O_2$ detection unit 112 and the concentration value of $H_2O_2$ vapor can then be established.

The valve 90 is allowed to remain open most of the time, but is generally closed when a low flow rate of air is required. If the flow rate of air is low, the valve 90 is closed and the air will flow only through the valves 94, 96, and 98. It should be noted that the valves 12, 16, 30, 34, and 60 are operated as required in order to set the conditions of flow rate and humidity and vary the quantity of $H_2O_2$ admitted to the system 10.

Additional temperatures 114a, 114b, and 114c can be used to monitor temperature in the test chamber 108 and in the titration station 100. A pressure sensor 116 can be used to monitor pressure in the test chamber 108. A Drager kit 118 can be used to detect the concentration of residual $H_2O_2$ vapor that exits the system 10.

The components of the system including, but limited to air conditioning components (e.g., pressure regulators, flow meters, dehumidifier(s), humidifier(s), heat exchangers), temperature sensors, humidity sensors, atomizer, metering pump, test cell, water bath, test chamber, titration station, and valves, are all commercially available. Optimal selection of these components can be made by one of ordinary skill in the art. While the sizes of the system 10 and the components thereof are not critical, the dimensions of a few components are given to provide an idea of the amount of space required for a calibration system. The size of the system 10 is about 3 meters×4 meters×3 meters. The size of the test cell 66 is about 1 foot×0.5 foot×0.5 foot. The size of the portable unit 112 is about 1 inch×2 inches×2 inches. The size of the Drager kit 118 is about 3 inches×3 inches×4 inches. The size of the test chamber 108 is about 8 inches high×about 4 inches in diameter. The volume of an impinger 102 is about 125 mL.

The operating conditions of the system can vary but they generally fall within the following ranges:

(a) temperature of the air ranges from about −10° C. to about 85° C.;

(b) relative humidity of the air ranges from about 10 to about 100%;

(c) the flow rate of air ranges from about 1 to about 200 cubic meters per hour;

(d) the concentration of sterilant ranges from 100 to 25000 ppm.

Calibration procedures should be conducted at regular time intervals to obtain reliable and accurate test results. The calibration system 10 can ensure the reliability and accuracy of the prediction of concentration of $H_2O_2$ determined by an $H_2O_2$ sensor by simulation of process conditions.

A series of calibration runs can be conducted for different temperature ranges, various $H_2O_2$ concentration levels, selected flow rates, adjusted relative humidity, different liquid $H_2O_2$ concentrations.

The method of this invention can be used to calibrate a sensor for a sterilization system to improve the ability to determine the concentration of sterilant at a given point in the system at any time at various processing stages. By this method, accurate information on the process at each stage can be provided.

The method of this invention can also be used to calibrate instruments for monitoring the concentration of $H_2O_2$ vapor in any environment where $H_2O_2$ vapor is employed. Such environments include, but are not limited to, clean room operations, pharmaceutical isolator sterilization, aseptic processing systems, and microbiological investigation of death rate for various bacteria under the effect of hydrogen peroxide.

This invention provides a method for calibrating instruments for determining the concentration of a sterilant, e.g., $H_2O_2$ vapor, for a wide range of processing and operating conditions. These operating condition include, but are not limited to, air temperature, flow rate of air, evaporation temperature, hydrogen peroxide injection rate, degree of saturation of air by hydrogen peroxide vapor at different temperatures, humidity variations, pressure fluctuations, etc.

It is to be understood that the method of this invention is not limited to the sterilant hydrogen peroxide. The method of this invention can be used to calibrate instruments for determining the concentration of other gases used for sterilization.

The following non-limiting example further illustrates the method of this invention.

EXAMPLE 1

The following example illustrates the calibration of a sensor by the method of this invention.

The system 10 shown in FIG. 1 was used to carry out the method of this example. When the system is activated, the valves 12, 16, 30, 34, and 60 are operated so as to deliver the desired quantities of air and $H_2O_2$ and the desired quality of air to the test cell 66. Because the test cell 66 is being used to calibrate a sensor 66, the valves 94, 96, and 98 are operated so that the air bypasses the test chamber 108. The valve 90 is allowed to remain open during the calibration runs of this example. Typical air quality conditions are 65% relative humidity, 70° C. Typical flow rates of air range from about 30 cubic meters/hour to about 110 cubic meters/hour.

Reference Calibration Data

Figure 3:
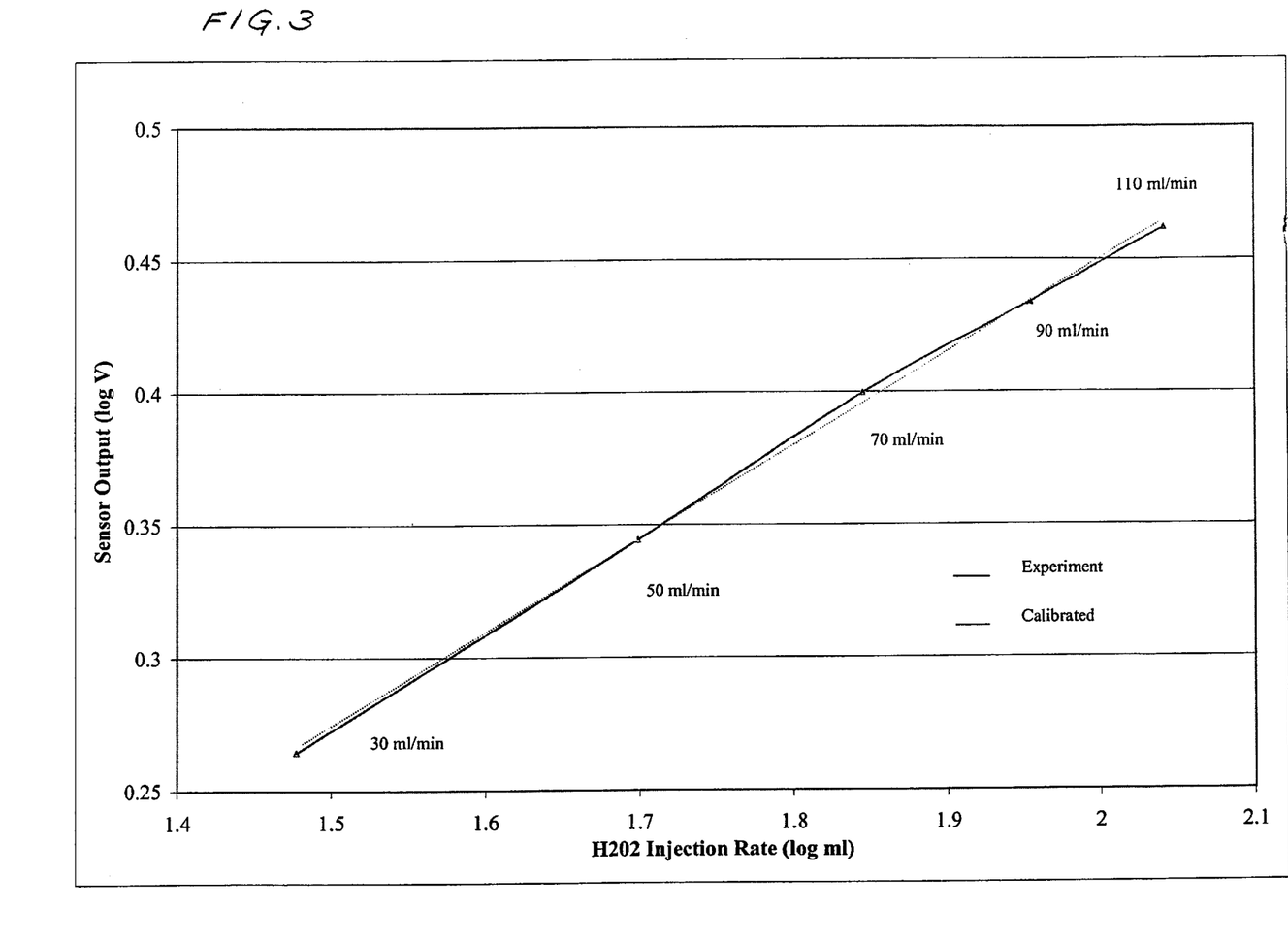
FIG. 3 illustrates a type of graph suitable for calibrating a sensor for use for detecting the concentration of hydrogen peroxide vapor in a system. The graph includes a reference calibration curve and a sensor calibration curve.

Fifteen (15) sensors (TGS 816, Figaro USA, Inc., Glenview, Ill. 60025) were used to prepare a linear reference calibration curve. This curve is described by the equation $y_1=a_1+b_1x$, where x represents concentrations of $H_2O_2$, $y_1$ represents the mean of the voltage readings taken at a particular value of concentration of $H_2O_2$ for the 15 sensors, $a_1$ represents the mean (average) of the intercepts of the plots of voltage v. concentration of $H_2O_2$ for the 15 sensors, and $b_1$ represents the mean (average) of the slopes of the plots of voltage v. concentration of $H_2O_2$ for the 15 sensors. See FIG. 3. The value of the slope and the value of the intercept of each of the 15 sensors were determined by data collected at at least three points (concentrations) on the abscissa. Each point was determined by at least two repetitions at each concentration. Table 1 is a compilation of the slopes and intercepts for each of the 15 sensors used to prepare the reference calibration data.

TABLE 1

| Sensor | Intercept | Slope |
| --- | --- | --- |
| 1 | −0.96 | 0.39 |
| 2 | −0.954 | 0.36 |
| 3 | −0.938 | 0.36 |
| 4 | −1.11 | 0.41 |
| 5 | −0.95 | 0.361 |
| 6 | −1.04 | 0.37 |
| 7 | −1.2 | 0.34 |
| 8 | −1.04 | 0.37 |
| 9 | −1.3 | 0.342 |
| 10 | −1.2 | 0.45 |
| 11 | −1.4 | 0.34 |
| 12 | −1.11 | 0.44 |
| 13 | −0.98 | 0.361 |
| 14 | −1.12 | 0.41 |
| 15 | −1.05 | 0.38 |

The data in Table 1 yielded a mean slope value (i.e., mean of $b_1$) of 0.379 and a mean intercept value (i.e., mean of $a_1$) of −1.090. The following table, Table 2, shows the relationship between voltage and concentration of $H_2O_2$ for reference calibration data utilizing the slope value of 0.379 and the value of −1.090, which were derived from the data in Table 1.

TABLE 2

| Concentration of $H_2O_2$ (ppm) | Voltage (volts) | Log (concentration of $H_2O_2$) | Log (voltage) |
| --- | --- | --- | --- |
| 3535 | 1.838 | 3.548 | 0.254 |
| 5839 | 2.210 | 3.766 | 0.337 |
| 8250 | 2.510 | 3.916 | 0.394 |
| 10607 | 2.715 | 4.026 | 0.435 |
| 12964 | 2.898 | 4.113 | 0.468 |

Sensor Calibration Data

One (1) sensor (TGS 816, Figaro USA, Inc., Glenview, Ill. 60025) was used to prepare a linear sensor calibration curve. This curve is described by the equation $y_2=a_2+b_2x$, where x represents concentrations of $H_2O_2$, $y_2$ represents the voltage reading taken at a particular value of concentration of $H_2O_2$ for a single sensor, $a_2$ represents the intersept of the plot of voltage v. concentration of $H_2O_2$ for the single sensor, and $b_2$ represents the slope of the plot of voltage v. concentration of $H_2O_2$ for the single sensor. See FIG. 3. The values of the slope and the intercept of the single sensor were determined by data collected at at least three points on the abscissa. Each point was determined by at least two repetitions at each concetration. The concentrations used are shown in Table 3.

TABLE 3

| Concentration of $H_2O_2$ (ppm) | Voltage (volts) | Log (concentration of $H_2O_2$) | Log (voltage) |
| --- | --- | --- | --- |
| 3535 | 1.838 | 3.548 | 0.264 |
| 5839 | 2.210 | 3.766 | 0.344 |
| 8250 | 2.510 | 3.916 | 0.400 |
| 10607 | 2.715 | 4.026 | 0.434 |
| 12964 | 2.898 | 4.113 | 0.462 |

The data in table 3 yielded a slope value of 0.351 and an intercept value of −0.098.

Normalizing

The following mathematical relationships were used to convert readings from an individual sensor to standardized values based on the reference calibration data. In the equations that follows, "voltage$_r$" means voltage of a point on the reference calibration curve, "voltage$_s$" means voltage of a point on the sensor calibration curve, "concentration$_r$" means concentration of a point on the reference calibration curve, and concentration$_s$" means concentration of a point on the sensor calibration curve.

Reference calibration curve:

$$\text{Log (voltage}_r) = -1.090 + 0.379 \text{ Log (concentration)}$$

Sensor calibration curve:

$$\text{Log (voltage}_s) = -0.981 + 0.352 \text{ Log (concentration}_s)$$

$$\text{Log (concentration}_s) = [\text{Log (voltage}_s) + 0.981]/0.352$$

Substituting the equivalent of Log (voltage$_s$) into the equation for Log (voltage$_r$) yields:

$$\text{Log (voltage}_r) = -1.090 + 0.379 \times [\text{Log (voltage}_s) + 0.981]/0.352$$

Thus, one can convert voltage data obtained from an individual sensor to a value of concentration on the reference curve. In order to compare several sensors, Table 4 shows values encountered in a typical conversion from the value of output voltage of a sensor to a value of voltage on the reference calibration curve, which value corresponds to a specific concentration of $H_2O_2$ vapor.

TABLE 4

| Concentration of $H_2O_2$ | Log (concentration of $H_2O_2$) | Voltage (ref[1]) | Log (voltage - ref) | Voltage (sen[2]) | Log (voltage - sen) | Log (voltage converted from voltage (sen)) |
| --- | --- | --- | --- | --- | --- | --- |
| 6000 | 3.778 | 2.196 | 0.342 | 2.224 | 0.347 | 0.342 |
| 8000 | 3.903 | 2.448 | 0.389 | 2.461 | 0.391 | 0.389 |
| 10000 | 4.000 | 2.664 | 0.426 | 2.662 | 0.425 | 0.426 |
| 12000 | 4.079 | 2.855 | 0.456 | 2.838 | 0.453 | 0.456 |
| 14000 | 4.146 | 3.027 | 0.481 | 2.996 | 0.477 | 0.481 |
| 16000 | 4.204 | 3.184 | 0.503 | 3.140 | 0.497 | 0.503 |

[1] The values of voltage on the reference calibration curve correspond to concentrations obtained by using an equation derived from statistical analysis. The equation was a linear equation in which the slope and an intercept of a line could be determined.
[2] The values of voltage were obtained by an experiment in which the value of voltage corresponded to the concentration of $H_2O_2$.

The seventh column of Table 4 shows that for a given concentration of $H_2O_2$, the value of log (voltage) obtained by means of the method of this invention is equal to the value of log (voltage) of the reference calibration curve, as shown in the fourth column of Table 4. Thus, if an individual sensor give a voltage reading of 0.347 volt, the reading will be adjusted to 0.342 volt, which translates to a concentration of $H_2O_2$ of 6000 ppm. The method of this invention allows the use of a plurality of sensors to measure the concentration levels of sterilant by means of fixed reference calibration data, thereby reducing the number of data conversions encountered when numerous sensors are used. This feature is extremely useful when several sensors are used at the same time under actual sterilization conditions.

Various modifications and alterations of this invention will become apparent to those skilled in the art without departing from the scope and spirit of this invention, and it should be understood that this invention is not to be unduly limited to the illustrative embodiments set forth herein.

What is claimed is:

1. A method for calibrating a sensor that is used for measuring the quantity of a sterilant in a system for delivering said sterilant, said method comprising the steps of:
   (a) generating reference calibration data, said reference calibration data showing a mathematical relationship between a measurable parameter and a quantity of said sterilant, for a plurality of sensors;
   (b) generating sensor calibration data, said sensor calibration data showing a mathematical relationship between said measurable parameter and said quantity of said sterilant for an individual sensor; and
   (c) normalizing said sensor calibration data to compensate for the difference between said measurable parameter for said reference calibration data and said measurable parameter for said sensor calibration data, whereby data obtained by said individual sensor can be used to accurately determine said quantity of sterilant in said system.

2. The method of claim 1, wherein said reference calibration data is generated by a method comprising the steps of:
   (a) providing a plurality of sensors;
   (b) subjecting each of said plurality of sensors to at least two quantities of air, each of said at least two quantities of air having (1) a known quality and (2) a known concentration of sterilant vapor, said sterilant vapor having a known physical condition;
   (c) measuring signals emitted by each of said plurality of sensors, each of said signals being proportional to a concentration of sterilant vapor;
   (d) establishing a mathematical relationship between said signals emitted by each of said plurality of sensors and said concentrations of sterilant vapor for each of said plurality of sensors; and
   (e) establishing said reference calibration data by means of a statistical analysis of said signals emitted by each of said plurality of sensors and said concentrations of sterilant vapor for each of said plurality of sensors.

3. The method of claim 2, wherein temperature of air ranges from about −10° C. to about 85° C.

4. The method of claim 2, wherein relative humidity of air ranges from about 10 to about 100%.

5. The method of claim 2, wherein flow rate of air ranges from about 1 to about 200 cubic meters per hour.

6. The method of claim 2, wherein concentration of sterilant ranges from 100 to 25000 ppm.

7. The method of claim 2, wherein said sterilant is hydrogen peroxide.

8. The method of claim 1, wherein said sensor calibration data is generated by a method comprising the steps of:
   (a) providing a sensor;
   (b) subjecting said sensor to at least two quantities of air, each of said at least two quantities of air having (1) a known quality and (2) a known concentration of sterilant vapor, said sterilant vapor having a known physical condition;
   (c) measuring signals emitted by said sensor, each of said signals corresponding to a concentration of sterilant vapor; and
   (d) establishing a mathematical relationship between said signals emitted and said concentrations of sterilant vapor for said sensor.

9. The method of claim 8, wherein temperature of air ranges from about −10° C. to about 85° C.

10. The method of claim 8, wherein relative humidity of air ranges from about 10 to about 100%.

11. The method of claim 8, wherein flow rate of air ranges from about 1 to about 200 cubic meters per hour.

12. The method of claim 8, wherein concentration of sterilant ranges from 100 to 25000 ppm.

13. The method of claim 8, wherein said sterilant is hydrogen peroxide.

14. The method of claim 1, wherein said sensor calibration data is normalized to compensate for the difference between said measurable parameter for said reference calibration data and said measurable parameter for said sensor calibration data for said sensor by a method comprising the steps of:
   (a) selecting a concentration of sterilant vapor;
   (b) determining the value of said measurable parameter at which said concentration of said sterilant vapor obtained from said sensor calibration data equals said concentration of said sterilant vapor obtained from said reference calibration data;
   (c) adjusting the values measured by said individual sensor a sufficient amount to compensate for the deviation between said reference calibration data and said sensor calibration data.

15. A method for calibrating a sensor that is used for measuring the quantity of a sterilant in a system for delivering said sterilant, said method comprising the steps of:
   (a) preparing a reference calibration curve, said reference calibration curve having a slope and an intercept;
   (b) preparing a sensor calibration curve, said sensor calibration curve having a slope and an intercept;
   (c) normalizing said sensor calibration curve to compensate for (1) the difference between said slope of said reference calibration curve and said slope of said sensor calibration curve and (2) the difference between said intercept of said reference calibration curve and said intercept of said sensor calibration curve.

16. The method of claim 15, wherein said reference calibration curve is prepared by a method comprising the steps of:
   (a) providing a plurality of sensors;
   (b) subjecting each of said plurality of sensors to at least two quantities of air, each of said at least two quantities of air having (i) a known quality and (ii) a known concentration of sterilant vapor, said sterilant vapor having a known physical condition;
   (c) measuring said signals emitted by each of said plurality of sensors, each of said signals being proportional to said concentration of sterilant vapor;

(d) establishing a linear mathematical relationship between said signals emitted by each of said plurality of sensors and said concentrations of sterilant vapor for each of said plurality of sensors; and (e) establishing said reference curve by means of a statistical analysis of said signals emitted by each of said plurality of sensors and said concentrations of sterilant vapor for each of said plurality of sensors.

17. The method of claim 16, wherein temperature of air ranges from about −10° C. to about 85° C.

18. The method of claim 16, wherein relative humidity of air ranges from about 10 to about 100%.

19. The method of claim 16, wherein flow rate of air ranges from about 1 to about 200 cubic meters per hour.

20. The method of claim 16, wherein concentration of sterilant ranges from 100 to 25000 ppm.

21. The method of claim 16, wherein said sterilant is hydrogen peroxide.

22. The method of claim 15, wherein said sensor calibration curve is prepared by a method comprising the steps of:

(a) providing an individual sensor;

(b) subjecting said sensor to at least two quantities of air, each of said at least two quantities of air having (1) a known quality and (2) a known concentration of sterilant vapor, said sterilant vapor having a known physical condition;

(c) measuring said signals emitted by said sensor, each of said signals being proportional to said concentration of sterilant vapor; and (d) establishing a linear mathematical relationship between said signals emitted by said individual sensor and said concentrations of sterilant vapor for said individual sensor.

23. The method of claim 22, wherein temperature of air ranges from about −10° C. to about 85° C.

24. The method of claim 22, wherein relative humidity of air ranges from about 10 to about 100%.

25. The method of claim 22, wherein flow rate of air ranges from about 1 to about 200 cubic meters per hour.

26. The method of claim 22, wherein concentration of sterilant ranges from 100 to 25000 ppm.

27. The method of claim 22, wherein said sterilant is hydrogen peroxide.

28. The method of claim 15, wherein said sensor calibration curve is normalized to compensate for (1) the difference between said slope of said reference calibration curve and said slope of said sensor calibration curve and (2) the difference between said intercept of said reference calibration curve and said intercept of said sensor calibration curve by a method comprising the steps of:

(a) determining said intercept of said reference calibration curve;

(c) determining said intercept of said sensor calibration curve;

(d) determining said slope of said reference calibration curve;

(e) determining said slope of said sensor calibration curve;

(f) adjusting said sensor calibration curve, if necessary, in order to compensate for said difference between said intercept of said reference calibration curve and said intercept of said sensor calibration curve;

(g) adjusting said sensor calibration curve, if necessary, in order to compensate for said difference between said slope of said reference calibration curve and said slope of said sensor calibration curve.

* * * * *